(12) United States Patent
Okabe et al.

(10) Patent No.: US 7,869,966 B2
(45) Date of Patent: Jan. 11, 2011

(54) INSPECTION METHOD AND ITS APPARATUS, INSPECTION SYSTEM

(75) Inventors: Takafumi Okabe, Yokohama (JP); Shunji Maeda, Yokohama (JP); Kaoru Sakai, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 10/936,501

(22) Filed: Sep. 9, 2004

(65) Prior Publication Data

US 2005/0033538 A1 Feb. 10, 2005

Related U.S. Application Data

(63) Continuation of application No. 10/241,589, filed on Sep. 12, 2002, now Pat. No. 6,799,130.

(30) Foreign Application Priority Data

Sep. 13, 2001 (JP) ............................. 2001-278750

(51) Int. Cl.
*G01N 37/00* (2006.01)

(52) U.S. Cl. ...................................... 702/82

(58) Field of Classification Search ............. 702/33–36, 702/40, 1, 81–84, 108, 183–185; 324/500, 324/512; 300/500, 635; 714/724; 438/12
See application file for complete search history.

(56) References Cited

U.S. PATENT DOCUMENTS

| | | | | |
|---|---|---|---|---|
| 4,226,539 A * | 10/1980 | Nakagawa et al. | ........... | 356/445 |
| 4,559,603 A * | 12/1985 | Yoshikawa | ....................... | 716/5 |
| 4,803,734 A * | 2/1989 | Onishi et al. | ................ | 382/115 |
| 4,996,434 A * | 2/1991 | Tanaka | ..................... | 250/492.3 |
| 5,214,712 A * | 5/1993 | Yamamoto et al. | .......... | 382/149 |
| 5,680,207 A | 10/1997 | Hagiwara | | |
| 6,185,707 B1 * | 2/2001 | Smith et al. | .................. | 714/724 |
| 6,334,097 B1 * | 12/2001 | Yoshitake et al. | ........... | 702/185 |
| 6,347,150 B1 * | 2/2002 | Hiroi et al. | .................... | 382/149 |
| 6,400,839 B1 * | 6/2002 | Takayama | .................... | 382/145 |
| 6,456,951 B1 * | 9/2002 | Maeda et al. | .................. | 702/81 |
| 6,614,022 B2 * | 9/2003 | Hiroi et al. | ................... | 250/310 |
| 6,629,051 B2 * | 9/2003 | Tanaka | ......................... | 702/81 |
| 6,973,209 B2 * | 12/2005 | Tanaka | ......................... | 382/149 |

(Continued)

FOREIGN PATENT DOCUMENTS

JP 57044838 * 3/1982

(Continued)

*Primary Examiner*—Aditya Bhat
(74) *Attorney, Agent, or Firm*—Antonelli, Terry, Stout & Kraus, LLP.

(57) ABSTRACT

The present invention relates to a tool for analyzing by priority a defect having a high possibility of causing an electrical failure when inspecting a particle and a pattern defect in a piece of work which constitutes an electronic device such as a semiconductor integrated circuit, and relates to a system therefor. On the basis of the result of comparison between defect information which is the result of inspection by an inspection tool and layout data stored in an auxiliary storage device, or on the basis of the result of reinspection by comparison between a defect and a wiring pattern as a background by an inspection processing operation unit, an object to be reviewed is selected using review conditions stored in the auxiliary storage device.

22 Claims, 15 Drawing Sheets

U.S. PATENT DOCUMENTS

| | | | |
|---|---|---|---|
| 6,987,873 B1 * | 1/2006 | Ben-Porath et al. | 382/145 |
| 7,283,659 B1 * | 10/2007 | Bakker et al. | 382/149 |
| 2002/0052053 A1 * | 5/2002 | Ono et al. | 438/12 |
| 2002/0094120 A1 * | 7/2002 | Hiroi et al. | 382/149 |
| 2003/0093767 A1 * | 5/2003 | Murai et al. | 716/21 |
| 2003/0195712 A1 * | 10/2003 | Ono et al. | 702/81 |
| 2004/0028272 A1 * | 2/2004 | Hiroi et al. | 382/162 |

FOREIGN PATENT DOCUMENTS

| | | |
|---|---|---|
| JP | 10-214868 | 8/1998 |
| JP | 2000-88583 | 3/2000 |
| JP | 2000-294611 | 10/2000 |
| JP | 2000-306964 | 11/2000 |
| JP | 2001-230289 | 8/2001 |

* cited by examiner

| NUMBER, | CHIP ROW, | CHIP LINE, | X, | Y, | DEFECT SIZE | ... |
|---|---|---|---|---|---|---|
| 1, | 2, | 2, | 73, | 67, | 2.4 | ... |
| 2, | 6, | 2, | 25, | 89, | 0.3 | ... |
| 3, | 5, | 3, | 47, | 69, | 1.5 | |
| 4, | 3, | 4, | 80, | 82, | 1.0 | |
| 5, | 6, | 4, | 52, | 78, | 1.2 | |
| 6, | 1, | 5, | 71, | 32, | 0.2 | |
| 7, | 4, | 6, | 87, | 90, | 0.7 | |
| 8, | 7, | 6, | 77, | 38, | 0.3 | |
| 9, | 3, | 7, | 83, | 45, | 0.8 | |
| 10, | 4, | 8, | 49, | 9, | 1.9 | |

21

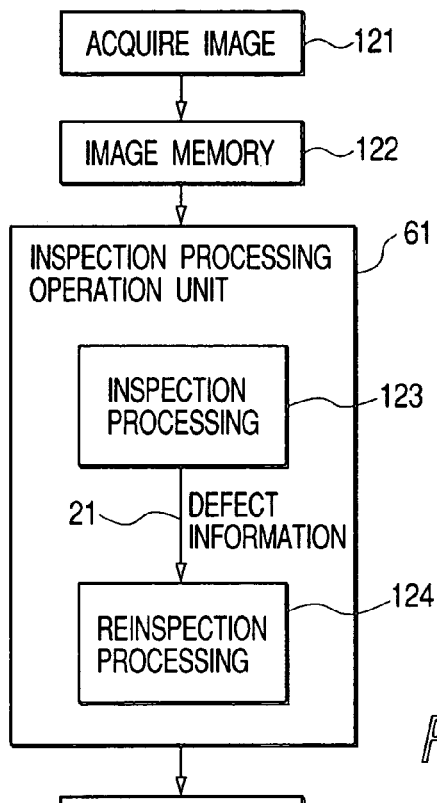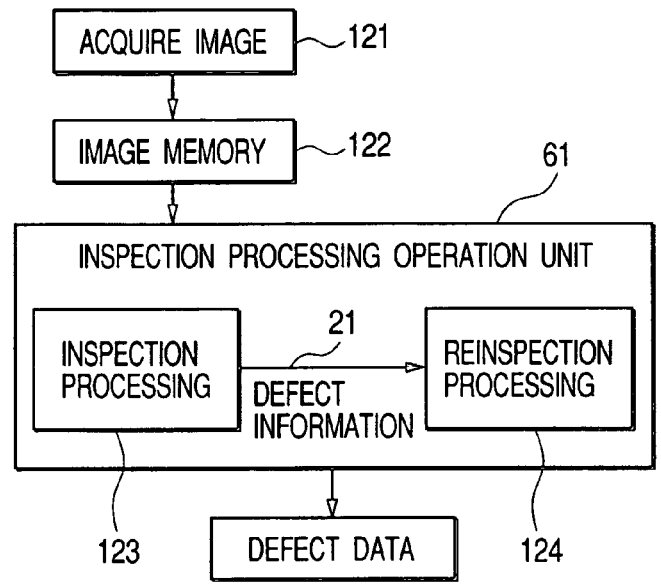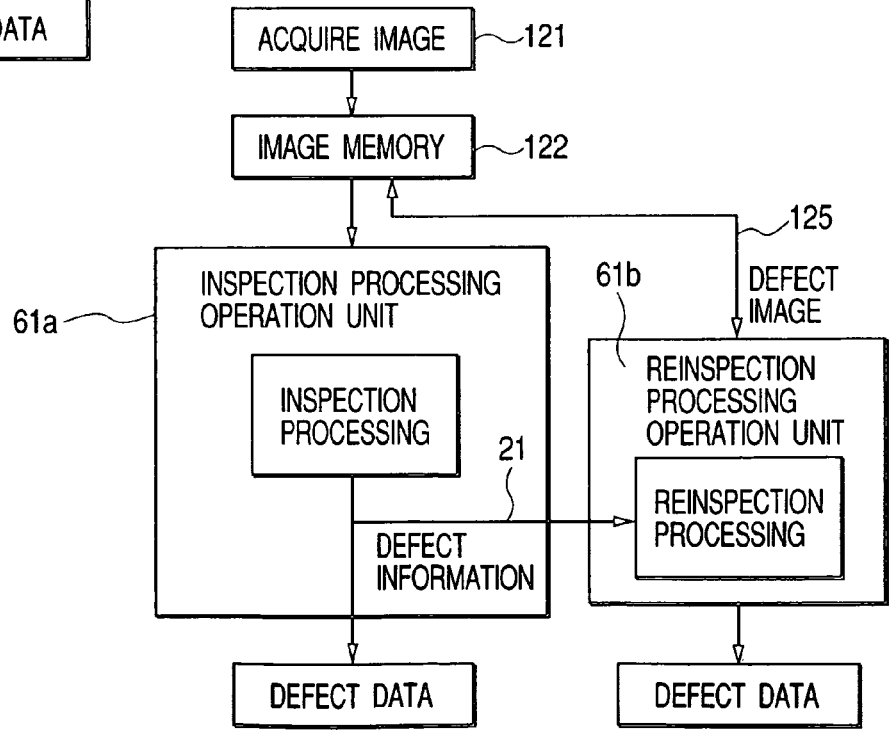

FIG. 14

EXAMPLE OF LABEL SETTING CRITERION INPUT SCREEN — 140

DEFECT CLASSIFICATION CRITERION

| | LINE WIDTH (μm) | | DEFECT SIZE (μm) | |
|---|---|---|---|---|
| LABEL 1 | 0.00 ~ | 0.20 | 0.00 ~ | 0.10 |
| LABEL 2 | 0.00 ~ | 0.20 | 0.10 ~ | 0.20 |
| LABEL 3 | 0.00 ~ | 0.20 | 0.20 ~ | |
| LABEL 4 | 0.20 ~ | 0.50 | 0.00 ~ | 0.20 |
| LABEL 5 | 0.20 ~ | 0.50 | 0.20 ~ | 0.35 |
| LABEL 6 | 0.20 ~ | 0.50 | 0.35 ~ | 0.50 |
| LABEL 7 | 0.20 ~ | 0.50 | 0.50 ~ | 1.00 |
| LABEL 8 | 0.20 ~ | 0.50 | 1.00 ~ | |

OTHER LABELS

CONSISTENCY CHECK — 141

OK    CANCEL    STANDARD    APPLY

EXECUTE CONSISTENCY CHECK AS TO WHETHER OR NOT THE LABEL
CONDITIONS WHICH HAVE BEEN SET OVERLAP ONE ANOTHER AND
WHETHER OR NOT THE SETTINGS LACK A REQUIRED LABEL CONDITION

FIG. 15

EXAMPLE OF REVIEW
ORDER SETTING SCREEN

PRIORITY ORDER OF REVIEW

| NO. 1 | LABEL 3 ▽ |
| NO. 2 | LABEL 4 ▽ |
| NO. 3 | LABEL 2 ▽ |
| NO. 4 | LABEL 5 ▽ |
| NO. 5 | LABEL 6 ▽ |
| NO. 6 | NIL ▽ |
| NO. 7 | NIL ▽ |

[APPLY]   [RETURN]

FIG. 16

EXAMPLE OF REVIEW
LABEL SELECTION SCREEN

EXECUTE REVIEW

|  | YES | NO |
|---|---|---|
| LABEL 1 | ◎ | ◎ |
| LABEL 2 | ◎ | ◎ |
| LABEL 3 | ◎ | ◎ |
| LABEL 4 | ◎ | ◎ |
| LABEL 5 | ◎ | ◎ |
| LABEL 6 | ◎ | ◎ |

OTHER LABELS ▽

[APPLY]   [RETURN]

FIG. 17

EXAMPLE OF REVIEW CONDITION SETTING SCREEN

| | NUMBER OF DETECTED DEFECTS | | SELECT | REVIEW ORDER | NUMBER OF DEFECTS TO BE REVIEWED |
|---|---|---|---|---|---|
| LABEL 1 | 189 | | ◎ | | 20 |
| LABEL 2 | 1135 | | ◎ | 3 | 60 |
| LABEL 3 | 230 | | ◎ | 1 | 20 |
| LABEL 4 | 50 | | ◎ | 2 | 10 |
| LABEL 5 | 3 | | ◎ | 4 | 3 |
| LABEL 6 | 35 | | ◎ | 5 | 7 |
| LABEL 7 | 60 | | ◎ | | 20 |
| LABEL 8 | 0 | | ◎ | | 20 |
| TOTAL | 2000 | | | TOTAL | 100 |

REVIEW SETTINGS

[OTHER LABELS]  [OK]  [CANCEL]  [STANDARD]  [APPLY]

INSPECTION METHOD AND ITS APPARATUS, INSPECTION SYSTEM

This application is a continuation of application Ser. No. 10/241,589 filed on Sep. 12, 2002 (now U.S. Pat. No. 6,799,130). The contents of application Ser. No. 10/241,589 are hereby incorporated herein by reference in their entirety.

BACKGROUND OF THE INVENTION

The present invention relates to an inspection method used in a production process of an electronic device such as a semiconductor integrated circuit, and relates to an inspection apparatus or inspection tool and an inspection system, which are used for realizing the inspection method, and a manufacturing method of a semiconductor device.

In the production of an electronic device typified by a semiconductor integrated circuit, after a defect is detected by darkfield and brightfield inspection tools, the detected defect is often reviewed in order to analyze an individual detected defect using a defect review function provided in the inspection tool itself or a dedicated image acquiring tool, such as a review apparatus or review tool, having an electron microscope, etc.

It is to be noted that the darkfield inspection tool detects a particle adhered to a wafer whereas the brightfield inspection tool detects a particle and a pattern defect formed on the wafer. Hereinafter the particle and the pattern defect are generically referred to as defect.

As compared with the darkfield and brightfield inspection tools, the review tool picks up a position of an individual defect as a high-resolution image. Accordingly, the review tool does not pick up all defect positions detected by the inspection tool, but samples the defect positions on a surface of a wafer to limit the number of defect positions to a few before picking up an image.

Conventionally, random sampling was used for the above-mentioned sampling; more specifically, a defect was selected at random from among the detected defects.

In addition, Japanese Patent Laid-open No. Hei 10-214866 discloses a technology in which, if there is a cluster-like defect such as a flaw or closely formed defects, classifying defects detected by an inspection tool into defects inside the cluster-like defect and defects outside the cluster-like defect. Even in such a case, a few defects are sampled at random from among the defects inside the cluster-like defect; and likewise, a few defects are sampled at random from among the defects outside the cluster-like defect.

Although it was possible to grasp statistically a tendency of defects using the conventional random sampling, a necessary defect was not efficiently reviewed. For example, measures could not be taken by priority against a critical defect causing an electrical failure; with the result that it was difficult to improve a yield effectively.

Moreover, with the microminiaturization of a circuit pattern of a semiconductor, the size of a detectable defect, required for an inspection tool, becomes smaller. For this reason, performance of the inspection tool is being enhanced accordingly, leading to an increase in the number of defects to be detected. Therefore, establishment of an effective reviewing method is desired.

SUMMARY OF THE INVENTION

The present invention provides an inspection method that can judge a defect which should be reviewed by priority so as to improve efficiency in inspection, and also provides a tool therefor.

Further, the present invention provides a manufacturing method of a semiconductor device that can take measures against a failure efficiently to improve a yield of the semiconductor device by judging a defect which should be reviewed by priority so as to improve efficiency in inspection.

To be more specific, the present invention is characterized in that paying attention to the relation between a defect size and a layout of a LSI chip, or the relation between a defect and a wiring pattern, a defect which should be reviewed by priority is select.

FIG. 9 illustrates a positional distribution of defects in a chip observed after an inspection tool detects the defects.

In this figure, data 35 of the defects detected by the inspection tool is plotted on a schematic diagram 32 illustrating a design circuit layout of the LSI chip. To be more specific, the detected defects are plotted according to position coordinates in respective LSI chips on a wafer. Each black dot indicates an individual defect. Rectangular frames B1 through B7 indicate positions of LSI block 1 through LSI block 7, respectively. Here, the LSI blocks include, for example, an A/D conversion block, a D/A conversion block, a memory block, and a processor block if the LSI blocks relate to a LSI used for a cellular phone. The LSI block is called a circuit block in general. Each LSI block has an independent function inside a LSI, and its placement also differs from the other except wiring connections.

As shown in the figure, the distribution of the defects detected by the inspection tool closely relates to a circuit layout, and has the following tendencies:

(1) The defect density differs according to roughness and fineness of a circuit layout. Depending on a kind of the inspection tool, the number of defects detected in an area where a circuit layout is rough is greater than the number of defects detected in an area where a circuit layout is fine. In general, roughness and fineness of circuit patterns differ on a LSI block basis; for example, a wiring width of a processor block is narrower than that of a memory block. Therefore, if a layout becomes dense, the inspection tool detects more defects in the processor block in comparison with the memory block.

(2) At edges (outlines) of the LSI block in the circuit layout, many defects are detected. The reason why this phenomenon occurs is that the inspection tool often detects a defect which is not a real defect by mistake. The inspection tool tends to detect such a false defect in a portion where a difference in unevenness of circuit patterns is large. In this case, an edge (outline) is a border between circuit blocks, and has a width ranging from tens to hundreds of micrometers.

In view of the foregoing, according to the present invention, a defect to be reviewed is selected using a LSI design layout in order to achieve the above-mentioned purpose. To be more specific, a defect which is not close to LSI block outlines is reviewed by priority using LSI design layout information; and a defect in a LSI block, a wiring width of which is narrow, is reviewed by priority.

Moreover, as shown in FIG. 11, it is also possible to judge the criticality of a defect with higher accuracy by using a wiring pattern image as a substitute for the design layout information to examine directly the relation between the wiring pattern image and the defect in detail.

This permits a defect which has a high possibility of influencing a yield to be efficiently reviewed by priority, whereby a direct factor exerting the influence can be identified in a short period of time and measures against the factor can easily be taken. Consequently, time taken to produce a defective unit is shortened, which leads to improvement in yield.

As is the case with a system LSI in particular, for a LSI item in which various circuit blocks exist, judging a defect which should be reviewed by priority is essential to an early improvement in yield.

These and other objects, features and advantages of the invention will be apparent from the following more particular description of preferred embodiments of the invention, as illustrated in the accompanying drawings.

BRIEF DESCRIPTION OF THE DRAWINGS

FIG. 12 is a diagram illustrating one embodiment of a method for performing reinspection processing;

FIG. 14 is a diagram illustrating an example of a label setting criterion input screen according to the present invention;

FIG. 15 is a diagram illustrating an example of a review order setting screen according to the present invention;

FIG. 16 is a diagram illustrating an example of a review label selection screen according to the present invention;

FIG. 17 is a diagram illustrating an example of a review condition setting screen according to the present invention;

DESCRIPTION OF THE PREFERRED EMBODIMENTS

Figure 1:
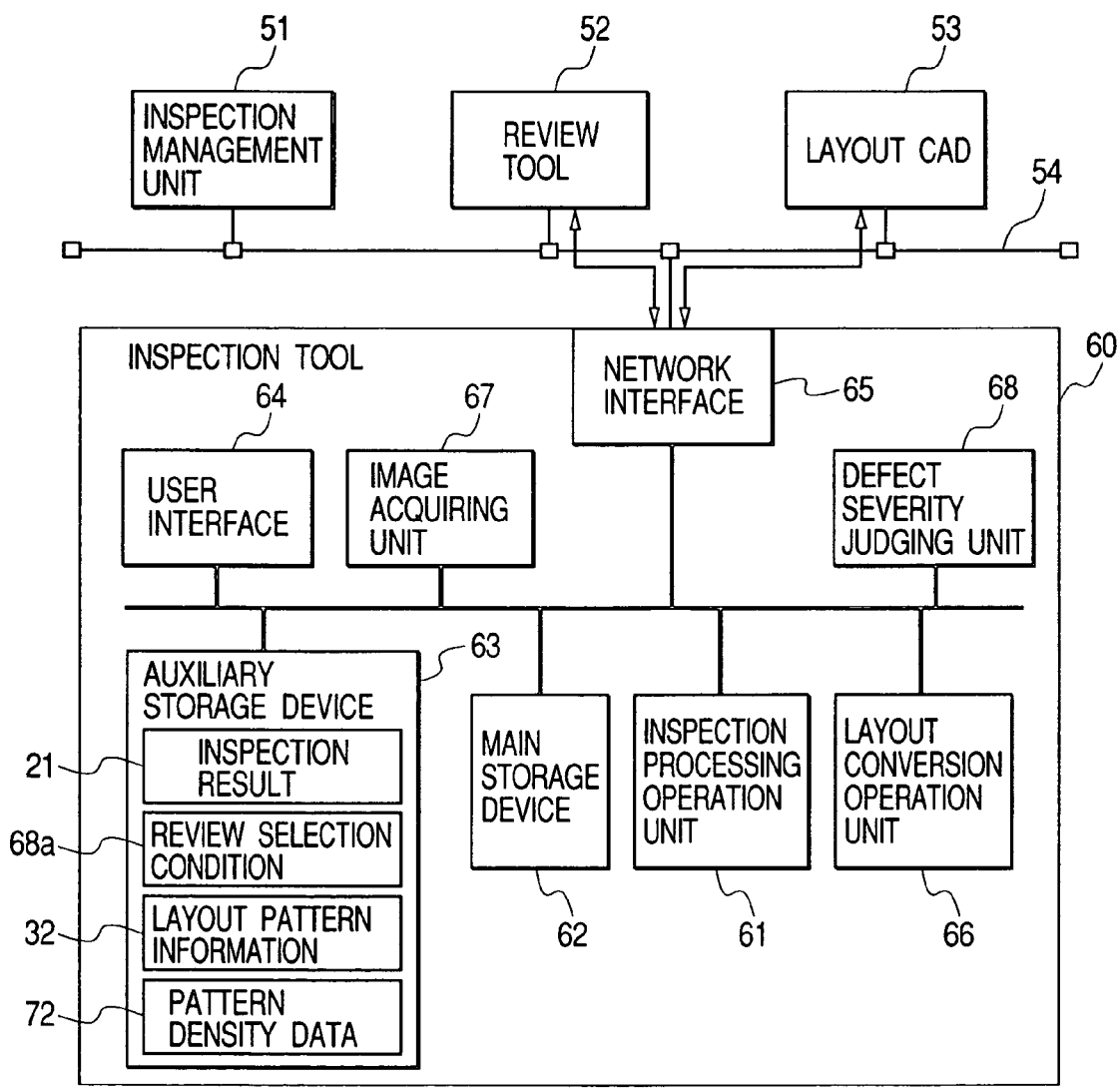
FIG. 1 is a block diagram illustrating one embodiment of a system configuration according to the present invention.

Preferred embodiments of a method for inspecting a semiconductor device and its tool, and preferred embodiments of a method for manufacturing the semiconductor device, according to the present invention, will be described below with reference to the drawing.

Figure 9:
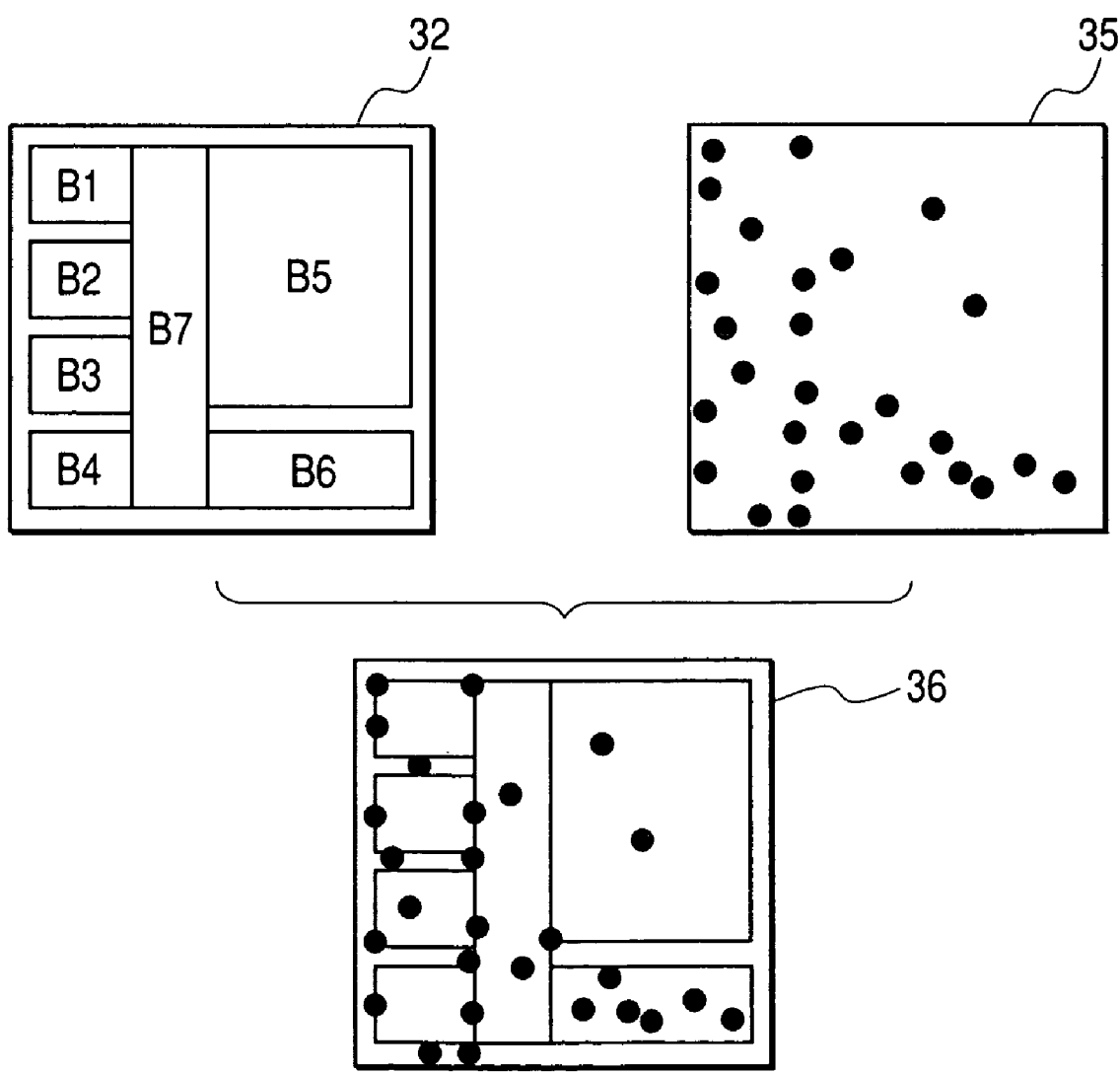
FIG. 9 is a diagram illustrating an example of a distribution of defect positions in a chip observed after the defects are detected by an inspection tool according to the present invention.

FIG. 9 illustrates a distribution map 36 showing how positions of defects detected by an inspection-processing unit 61 of an inspection tool 60 in a configuration shown in FIG. 1 are distributed in a chip. This distribution map 36 showing the defect positions distributed in the chip is made by plotting data 35 of the detected defects on a schematic diagram 32 illustrating a circuit layout of a LSI chip. To be more specific, the detected defects are plotted according to position coordinates in respective LSI chips on a wafer. Each black dot indicates an individual defect. Rectangular frames B1 through B7 indicate positions of LSI function block 1 through LSI function block 7, respectively. Here, the LSI function blocks include, for example, an A/D conversion block, a D/A conversion block, a memory block, and a processor block if the LSI blocks relate to a LSI used for a cellular phone. The LSI function block is called a circuit block in general. Each LSI function block has an independent function inside a LSI, and its placement also differs from others except wiring connections.

As shown in the figure, the distribution of the defects detected by the inspection tool 60 closely relates to a circuit layout, and has the following tendencies:

(1) The defect density differs according to roughness and fineness of a circuit layout. Depending on a kind of the inspection tool 60, the number of defects detected in an area where a circuit layout is rough is greater than the number of defects detected in an area where a circuit layout is fine. In general, roughness and fineness of circuit patterns differ on a LSI function block basis; for example, a wiring width of a processor block is narrower than that of a memory block. Therefore, if a layout becomes dense, the inspection tool 60 detects more defects in the processor block in comparison with the memory block.

(2) At edges (outlines) of the LSI function block in the circuit layout, many defects are detected. The reason why this phenomenon occurs is that the inspection tool 60 often detects, by mistake, a defect which is not a real defect. The inspection tool 60 tends to detect such a false defect in a portion where a difference in unevenness of circuit patterns is large. In this case, an edge (outline) is a border between circuit function blocks, and has a width ranging from tens to hundreds of micrometers.

For this reason, in the present invention, a defect to be reviewed is selected using a LSI design layout. To be more specific, a defect which is not close to LSI block outlines is reviewed by priority using LSI design layout information; and a defect in a LSI block, a wiring width of which is narrow, is reviewed by priority.

FIG. 1 is a block diagram illustrating one embodiment of a configuration of a semiconductor device inspection system according to the present invention.

The semiconductor device inspection system according to the present invention comprises an inspection tool 60, a review tool 52, an inspection management unit 51, and a layout CAD 53. The inspection tool 60 includes a brightfield inspecting tool (including an optical tool or a SEM, which is used for inspection of an improperly shaped circuit pattern), and an optical darkfield inspection tool used for particle detection. The review tool 52 reviews a defect on the basis of information, obtained from the inspection tool 60, about a defect which should be reviewed by priority. The inspection management unit 51 includes a data analyzing system which supports an improvement in yield by collecting data, etc., obtained from the tools including the inspection tool 60, the review tool 52, a measuring instrument, and a tester, relating to inspection, measurement, review, and analysis, and by managing and analyzing them synthetically. The layout CAD 53 creates data of layout CAD. The inspection tool 60, the review tool 52, the inspection management unit 51, and the layout CAD 53 are connected to one another via a LAN (network) 54 so that data can be exchanged as the need arises.

The inspection tool 60 comprises an image-acquiring unit 67, an inspection processing operation unit 61, a layout conversion operation unit 66, a defect severity-judging unit 68, a main storage device 62, an auxiliary storage device 63, and a network interface 65. They are connected through buses.

In the configuration, the image-acquiring unit 67 illuminates a light beam, which includes UV light and DUV light, or a charged particle beam on an object to be inspected such as a semiconductor wafer where a LSI such as a system LSI is formed. After that, the image acquiring unit 67 detects reflected light, or a reflected or transmitted charged particle, coming from the object to be inspected, using a detector, and then acquires a detected defect image including a circuit pattern defect, a particle, and a flaw, generated on the object to be inspected, before storing the defect image into, for example, the main storage device 62.

In addition, the inspection processing operation unit 61 aligns the detected image (obtained by the image acquiring unit 67, and stored into an image memory before outputting) with a reference image, and then compares them to detect a mismatch as a defect. After that, the inspection processing operation unit 61 detects inspection result data 61a including a position of the detected defect and its size (an area, a projected length with reference to the X, Y axes, etc.), and temporarily stores the inspection result data 61a in the main storage device 62 having, for example, a RAM before storing the data in the auxiliary storage device 63.

Figure 5:
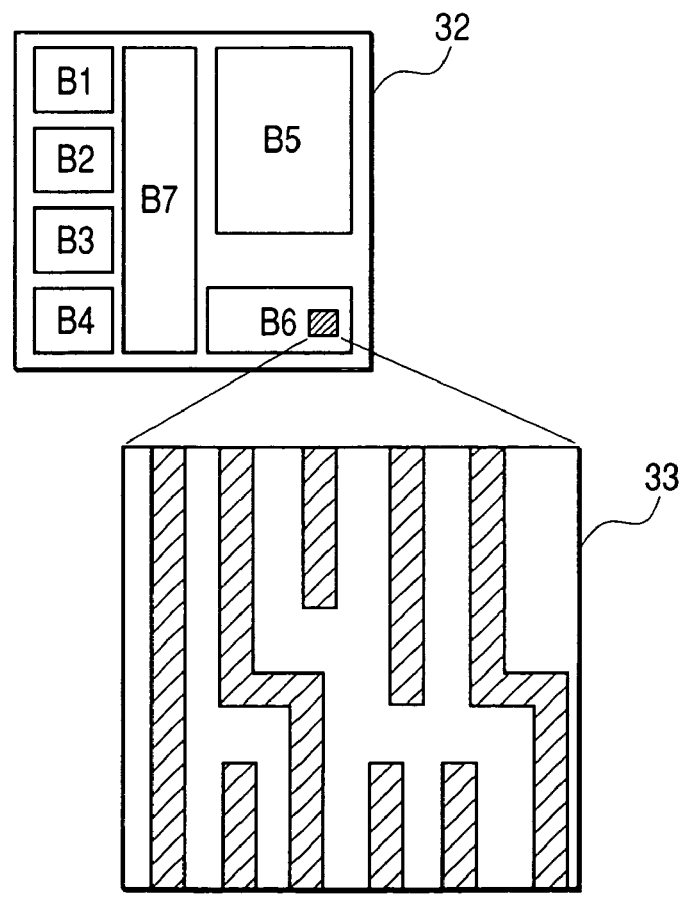
FIG. 5 is a diagram illustrating an example of circuit layout pattern information.
Figure 6:
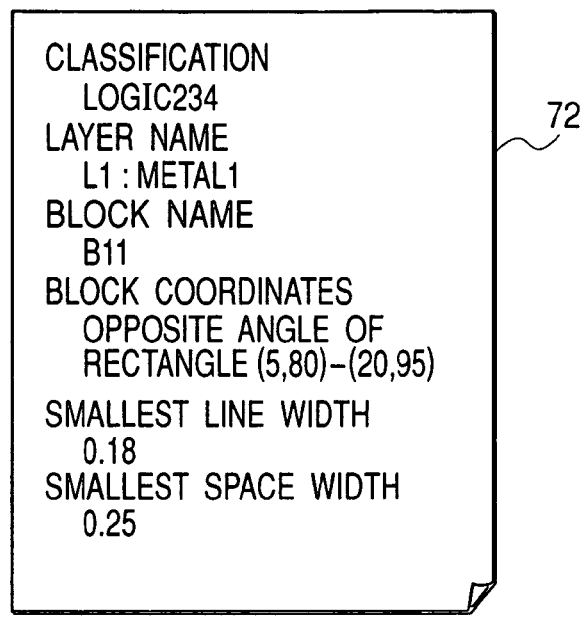
FIG. 6 is a diagram illustrating an example of a pattern density data file.

The layout conversion operation unit 66 creates circuit layout pattern information 32 shown in FIG. 5 and pattern density data 72 shown in FIG. 6 on the basis of CAD data obtained from the layout CAD 53, and then temporarily stores the circuit layout pattern information 32 and the pattern density data 72 in the main storage device 62 having, for example, a RAM before storing the information and the data in the auxiliary storage device 63.

On the basis of the inspection result data 21, the circuit layout pattern information 32 and the pattern density data 72, which have been stored in the auxiliary storage device 63, the defect severity judging unit 68 judges severity (criticality) of each defect according to a review selection condition program 68a. Next, the defect severity-judging unit 68 creates information about a defect which should be reviewed by priority, and then temporarily stores the defect information in the main storage device 62 such as a RAM, for example, before storing the defect information in the auxiliary storage device 63.

The main storage device 62 comprises the following: a user interface 64 comprising a display unit for displaying screens shown in FIGS. 13 through 17, and an inputting means; the above-mentioned RAM; a ROM in which programs executed in the inspection processing operation unit 61, the layout conversion operation unit 66, and the defect severity judging unit 68 are stored.

The auxiliary storage device 63 stores the inspection result data 61a, the review selection condition program 68a, the layout data 53a, and the pattern density data 72, all of which can also be recorded on a recording medium for output.

Moreover, the network interface 65 permits exchange of data between the inspection tool 60 and devices including the layout CAD 53, the review tool 52, and the inspection management unit 51 via the LAN 54.

The inspection tool 60 is a darkfield inspection tool or a brightfield inspection tool that calculates a coordinate position, and its size (an area, and a projected length with reference to the X, Y axes), of a defect on a surface of an object to be inspected such as a semiconductor wafer using, for example, the inspection processing operation unit 61, and that stores the result in the auxiliary storage device 63 as inspection result data 21. A classification, a lot number, a wafer number, a layer name and the like, are added to the inspection result data 21 (wafer map data) which includes information about the coordinate position, and the size, of the defect on the surface of the semiconductor wafer. Then, the data are stored in an inspection result database of the auxiliary storage device 63.

Figures 2, 3:
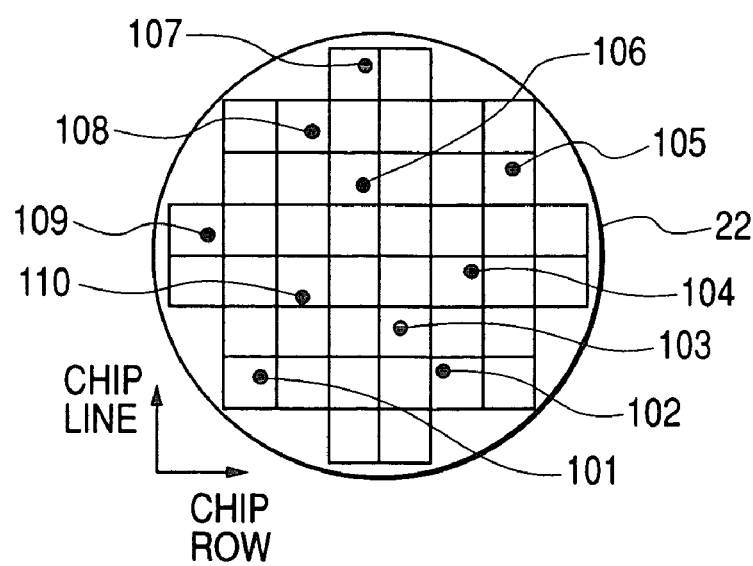
FIG. 2 is a diagram illustrating an example of wafer map data.
FIG. 3 is a diagram illustrating an example of a two-dimensional map of the wafer map data shown in FIG. 2.

FIG. 2 illustrates one embodiment of the wafer map data detected by the inspection processing operation unit 61 of the inspection tool 60. The wafer map data 21 has information about a coordinate position, and its size, of each defect on a wafer surface. In this embodiment, the wafer map data (inspection result data) 21 has a defect number, a chip row, a chip line, an X coordinate, a Y coordinate, the defect size (a dimension of a defect) and the like for each defect. The defect number is a serial number that is given to a defect detected by the inspection tool 60. The inspection operation-processing unit 61 automatically gives the defect number to the detected defect. The chip row, the chip line, the X coordinate, and the Y coordinate indicate a coordinate position of the defect. The chip line and the chip row indicate a position of a chip on a wafer; and the X coordinate and the Y coordinate indicate a defect position on the chip. It is to be noted that the chip row and the chip line are calculated in the inspection processing operation unit 61 using, for example, layout data of the chip. The defect size (a dimension of a defect) indicates, for example, an area S, and projected lengths (LX, LY) with reference to the X, Y axes, of the defect.

Figure 4:
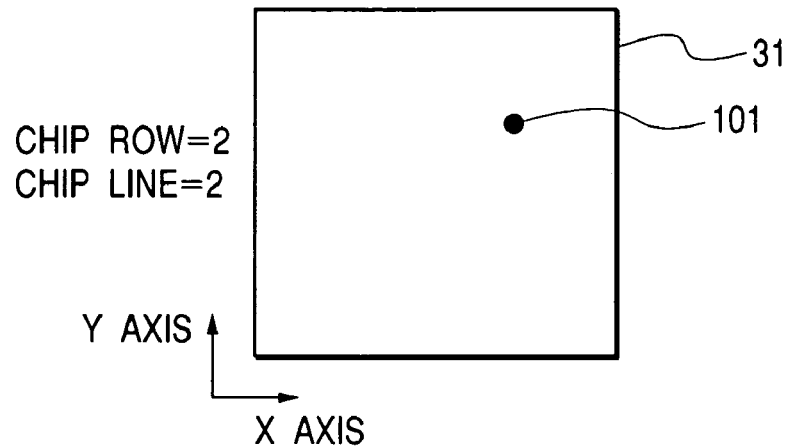
FIG. 4 is an enlarged view illustrating a chip row 1, a chip line 1 shown in FIG. 3.

To be more specific, the inspection-processing operation unit 61 creates the wafer map data 21, which describes a state shown in FIGS. 3 and 4, on the basis of an image acquired by the image-acquiring unit 67. FIG. 3 is a diagram in which the wafer map data 21 in FIG. 2 is illustrated as a two-dimensional map. A circle 22 represents a wafer; and rectangular frames inside the circle 22 represent respective chips. A chip row, and a chip line, of the wafer map data 21 indicate an arrangement of a chip relative to a wafer edge. Black dots from reference numerals 101 to 110 indicate positions of defects that have defect numbers 1 through 10 in the wafer map data 21, respectively. Each of the positions is based on a chip row, a chip line, an X coordinate, and a Y coordinate. FIG. 4 is an enlarged view illustrating a chip corresponding to chip row 2 and chip line 2 shown in FIG. 3. A rectangular frame 31 represents the chip. On the basis of X and Y coordinates of the wafer map data 21, reference numeral 101 indicates a position of the defect number 1 relative to the lower left edge as a starting point.

On the other hand, circuit layout data, the design of which has been completed by the layout CAD 53, is inputted into the inspection tool 60 via the LAN 54 together with a classification and a layer name, and is then stored in the auxiliary storage device 63 through the main storage device 62. For example, the layout conversion operation unit 66 generates position information of blocks B1 through B7 in the chip using the circuit layout data, and then stores the information in the auxiliary storage device 63 as circuit layout pattern information 32 through the main storage device 62. It is to be noted that the circuit layout pattern information 32 is not necessarily generated by the layout conversion operation unit 66 or the layout CAD 53, and that storing the circuit layout pattern information 32 in the auxiliary storage device 63 together with a classification and a layer name suffices.

In the auxiliary storage device 63, besides the above-mentioned information, a review selection condition program for selecting a defect, which should be reviewed in the defect severity judging unit 68, and the like, are stored as described below. It is to be noted that the auxiliary storage device 63 may store, for example, information about a defect to be reviewed by priority which the defect severity judging unit 68 has created by judging the severity of the defect.

Next, an example of the circuit layout pattern information 32 which is created by the layout conversion operation unit 66 on the basis of circuit layout data, and an example of the pattern density data 72, will be described with reference to FIGS. 5 and 6.

FIG. 5 illustrates an example of the circuit layout pattern information 32. Reference numeral 32 is a schematic diagram illustrating the circuit layout pattern information. Rectangular frames B1 to B7 indicate positions of LSI function blocks 1 through 7, respectively. Reference numeral 33 is an enlarged view of a part (a part shown with oblique lines in a rectangular frame) in B6. White parts in the enlarged view 33 are parts having no circuit pattern; and gray parts in the enlarged view 33 are circuit patterns.

FIG. 6 illustrates an example of the pattern density data 72. The pattern density data file 72 comprises the following information: a classification LOGIC234; a layer name of a layer L1 METAL1; the smallest line width and the smallest space width in a block name B11; and position information of the block B11. The pattern density data file 72 is stored in the auxiliary storage device 63 as pattern density data. In this connection, a column of "block coordinates" in FIG. 6 means that an area of the block name B11 has a rectangle shape and that coordinates of its opposite angle (position information) are X=5, Y=80 and X=20, Y=95 in a chip.

Next, the following processing will be described: for example, on the basis of the inspection result data 21, the circuit layout pattern information 32 and the pattern density data 72, which have been stored in the auxiliary storage device 63, the defect severity judging unit 68 judges severity (criticality) of each defect according to the review selection condition program 68a, creates information about a defect which should be reviewed by priority, and then temporarily stores the information in the main storage device 62 such as a RAM, for example, before storing the information in the auxiliary storage device 63.

Figure 7:
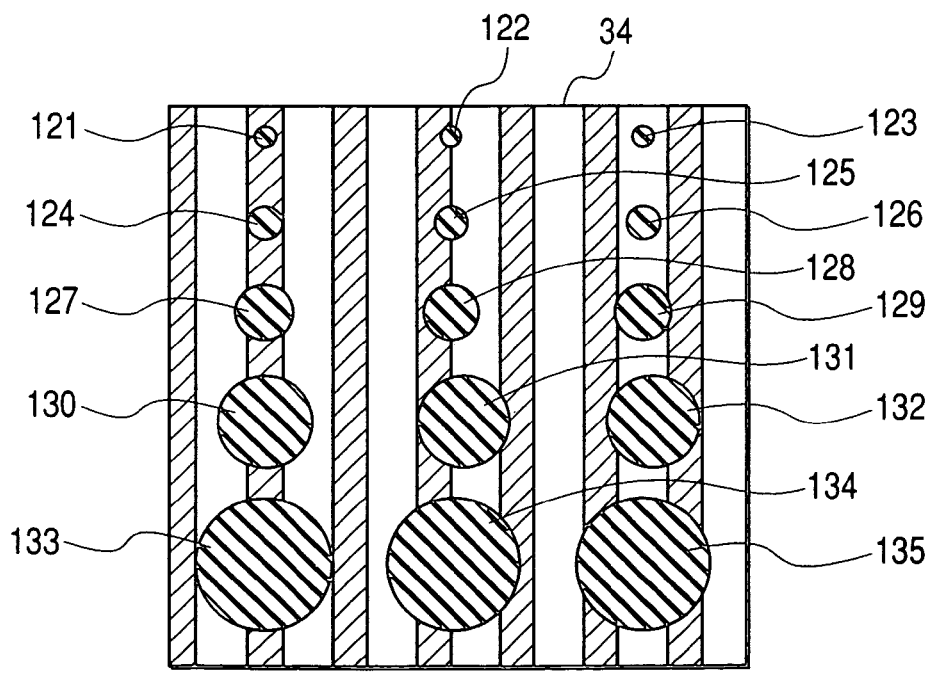
FIG. 7 is a diagram illustrating the relation between a circuit pattern (wiring pattern) and a defect size.

FIG. 7 is a diagram illustrating the relation between a circuit pattern and the defect size. Reference numeral 34 is an enlarged view in which circuit patterns and virtual defects are collated with each other. Reference numerals 121 through 135 represent the virtual defects (particles, pattern defects, etc.), which are used for analyzing a defect that will cause an electrical failure. The defects 121 through 123, the defects 124 through 126, the defects 127 through 129, the defects 130 through 132, or the defects 133 through 135, have the same defect size. Nevertheless, the defects occur at different positions relative to wiring patterns. An example of a defect classification method on the basis of defect sizes obtained from the inspection result 21 will be described with reference to this figure.

Because all defect sizes of the defects 121 through 123 are smaller than a pattern wiring width and a pattern space width, a possibility of causing a failure is low regardless of positions of the defects relative to the wiring patterns. Accordingly, the defects 121 through 123 having this size are treated as, for example, label 1.

Next, although the defects 124 through 126 are larger than the wiring width, they are smaller than the space width. Accordingly, there is a possibility that the defect 124 will cause a failure such as a break. However, as for the defects 125, 126, a possibility of causing a failure is low. For this reason, the defects 124 through 126 having this size are treated as, for example, label 2.

The defects 127 through 129 are larger than the line width and the space width. Accordingly, although there is a low possibility that the defect 128 will cause a failure, there is a possibility that the defect 127 is a break, and there is a high possibility that the defect 129 is an electrical short circuit failure. For this reason, the defects 127 through 129 having this size are treated as, for example, label 3.

The defects 130 through 132 are larger than the sum of the line width and the space width. Accordingly, there is a high possibility that the defect 130 is a break; and there is a high possibility that the defects 131, 132 are short circuit failures. For this reason, the defects 130 through 132 having this size are treated as, for example, label 4.

The defects 133 through 135 are large, and all of them are in contact with two or more pattern wires. Therefore, a possibility of a short circuit failure is high. The defects 133 through 135 having this size are treated as, for example, label 5.

Figure 8:
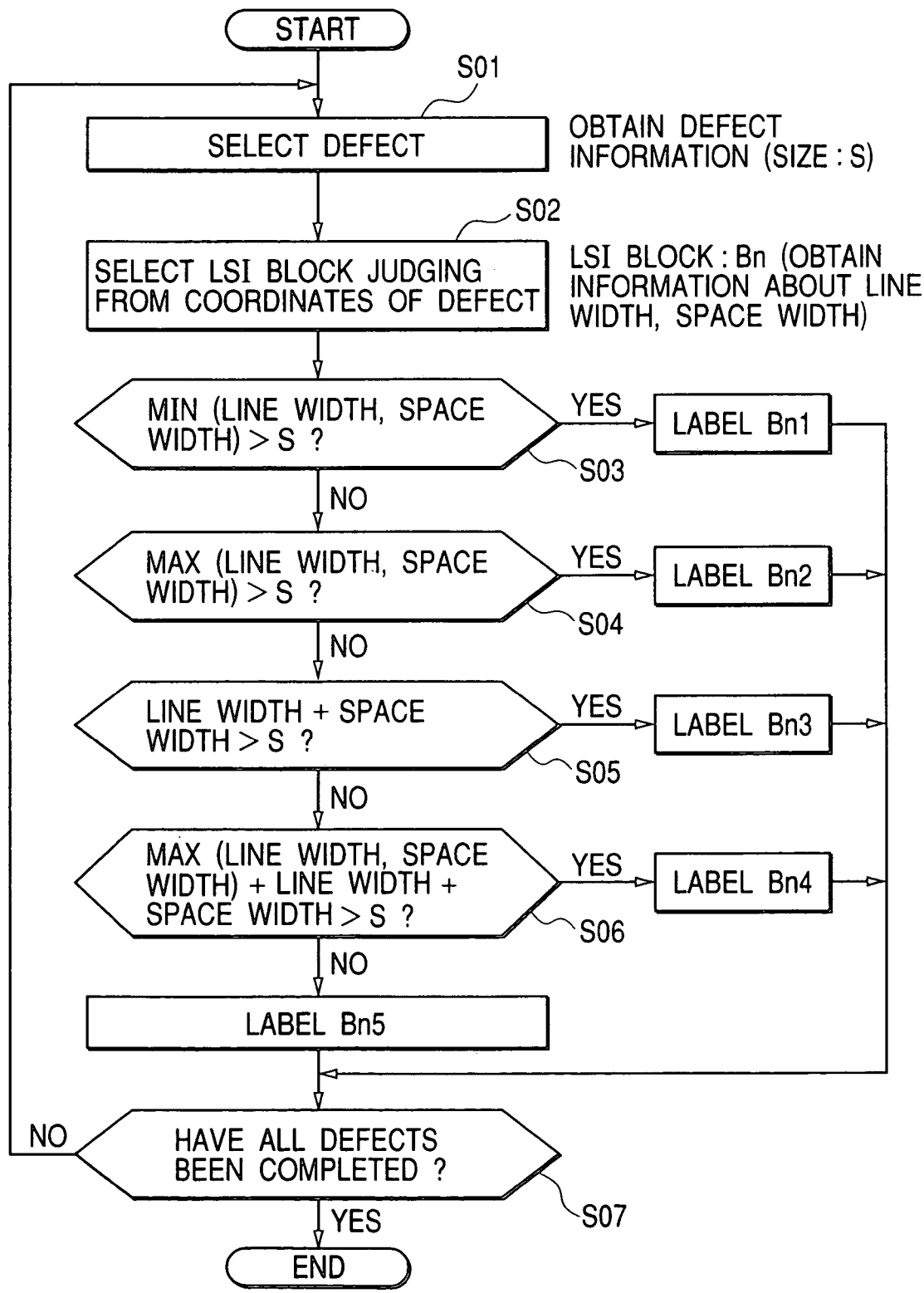
FIG. 8 is a diagram illustrating one embodiment of procedural steps of defect labeling according to the present invention.

Next, for example, one embodiment of procedural steps of labeling, which is used for selecting the priority order of review performed in the defect severity judging unit 68, will be described with reference to FIG. 8.

In the first place, for example, the defect severity judging unit 68 selects a defect one by one from among all defect information which is the inspection result 21 stored in the auxiliary storage device 63, and then obtains defect information including its coordinates and its size (S) (S01). Subsequently, for example, judging from the coordinates of the defect, the defect severity judging unit 68 selects a LSI function block Bn to which the defect belongs according to circuit layout pattern information stored in the auxiliary storage device 63, and then obtains pattern density data relating to the function block Bn (a line width, a space width, etc.) from the auxiliary storage device 63 (S02).

To begin with, for example, the defect severity-judging unit 68 compares line widths and space widths in the LSI function block, and selects a defect having a smaller size (MIN (line width, space width)). If the defect size (S) obtained from the inspection result 21 is smaller than the selected MIN (line width, space width), a label of this defect is treated as Bn1 (S03). If the defect size (S) is not smaller than the selected MIN, then the defect size (S) is compared with MAX (line width, space width)(S04). If the defect size (S) is smaller than MAX (line width, space width), this defect label is set at Bn2. Next, the defect size (S) is compared with the sum of the space width and the line width (S05). If the defect size (S) is smaller than the sum of the line width and the space width, this defect label is set at Bn3. If not, the process proceeds to the next step. The defect size (S) is compared with the sum of MAX (line width, space width), the line width, and the space width (MAX (line width, space width)+line width+space width) (S06). If the defect size (S) is smaller than (MAX (line width, space width)+line width+space width), the defect label is set at Bn4. If not, the defect label is set at Bn5.

As described above, for example, the defect severity judging unit 68 sets labels of all defects in the steps S01 through S06, and stores the result in the auxiliary storage device 63 for example. This permits all defects to be labeled according to the correlation of the defect size (S) with a line width and a space width in various LSI function blocks which constitute the chip 31 so that the priority order of review can be selected.

In the example of the labels which have been set in the above-mentioned manner, label 1 (Bn1) means that a possibility of a failure is low. The larger the label number increases, the higher a possibility of a failure becomes. As the uses of these labels, for example, the following methods can be considered: after selecting only defects having label 2 and label 3, using a review function of the inspection tool 60 to review the defects; if a defect having label 2, for example, cannot be sufficiently reviewed using the review function of the inspection tool 60, transferring defect coordinate data to another review tool 52 such as a dedicated SEM to review the defect using the dedicated review tool 52; and the like.

However, the priority order of review is not determined only by defect size (label) in various LSI function blocks which constitute the chip 31. The priority order also depends on the number of defects belonging to the label. To be more specific, even in the case of a label, a failure possibility of which is low, if the number of defects is large, an effect of an improvement in yield by analyzing the failures and taking measures against the failures can be expected. Therefore, this case is treated as a high priority order of review. For this reason, for example, the defect severity judging unit 68 calculates the number of defects belonging to the same label in various LSI function blocks which constitute the chip 31, and then stores the calculated number, for example, in the auxiliary storage device 63 as data used for selecting the priority order of review.

In addition, because a label is set on the basis of a position where a defect exists, to be more specific, on the basis of information about pattern wiring density, the number of classified labels may become several times as many as the number of labels described above. Therefore, reviewing steps and the priority order can be adjusted in more detail as follows: reviewing a defect in a LSI function block having high wiring density by priority; or the like.

Next, an embodiment in which accuracy in judgment of a failure can be improved by additionally performing reinspection processing for a defect image in the inspection processing operation unit 61 of the inspection tool 60 to examine the relation between a pattern and a defect in more detail will be described with reference to FIGS. 10 and 11.

Figure 10:
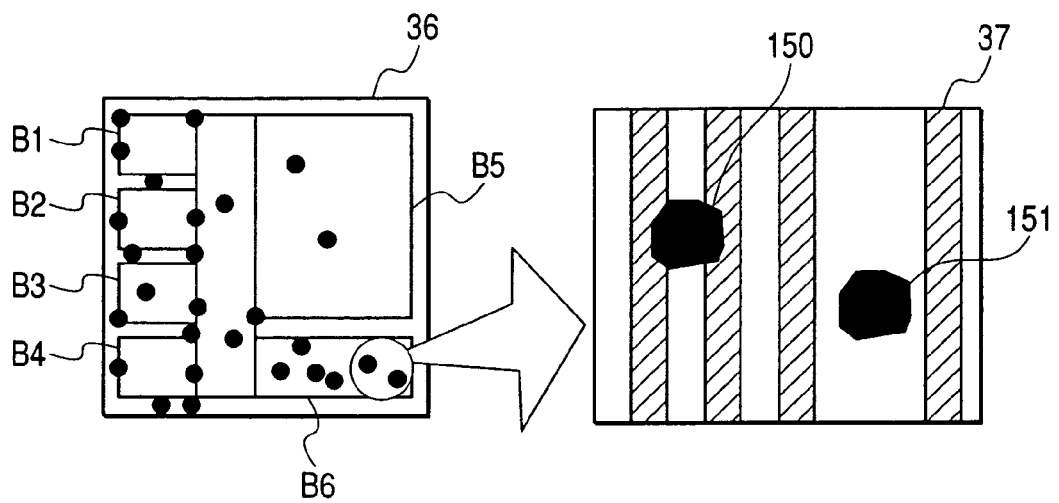
FIG. 10 is a diagram illustrating an example of a diagram that illustrates the relation between a defect and a wiring pattern which is a background.
Figure 11:
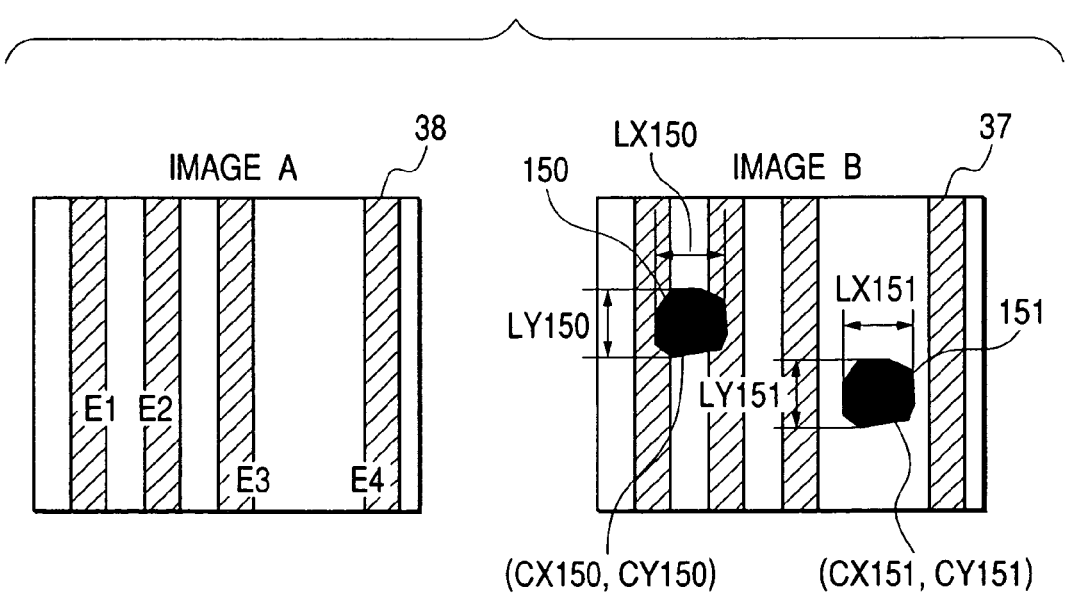
FIG. 11 is a diagram illustrating an example of a diagram that illustrates dimensions of a defect and a wiring pattern which is a background.

In FIG. 10, reference numeral 36 is a distribution map in which defect data is superimposed on a block diagram of LSI; and reference numeral 37 is a magnified view illustrating part of a block B6 in the distribution map 36.

As described above, the severity of a defect candidate is determined by the relation between a defect size and a wiring pattern that is a background. However, in the method for determining the circuit layout pattern information 32 and the pattern density data 72, the severity of a defect is judged by typical pattern information of a function block which includes the defect. Accordingly, accuracy in judgment is low; in other words, a probability is merely determined. For example, in the case of the enlarged view 37 shown in FIG. 10, although two defects 150, 151 having an equal size are included in the same block B6, wiring pattern spaces which are backgrounds of the defects differ. In this case, there is a high possibility that the defect 150 is a failure. On the other hand, there is an extremely low possibility that the defect 151 is a failure. Accordingly, labels to be added to both of the defects are distinguished; and high priority of review is given to the defect 150, and low priority of review is given to the defect 151. A defect like the defect 151 can also be eliminated from candidates.

In this connection, one embodiment of a method for examining the relation between a defect and a wiring pattern will be described with reference to FIG. 11.

To be more specific, inspection processing in the inspection processing operation unit 61 of the inspection tool 60 is performed by comparing two images, a detected image B and a reference image A, in which the same wiring pattern is picked up. As a result of the comparison of the images, a part where gray-scale difference is large is regarded as a defect candidate. As defect information (inspection-result information) 21, defect center coordinates (CX, CY), defect size (area S; X, Y lengths LX, LY; etc.) are determined.

In this embodiment, for example, the inspection processing operation unit 61 performs reinspection processing for its defect candidate using an image having an appropriate size which includes coordinates of the defect stored in an image memory. Between the two images, the number of image which includes the defect is only one, that is to say, the detected image B (reference numeral 37 in FIG. 11). In the other image (the reference image A), a part corresponding to the defect includes only wiring patterns (reference numeral 38 in FIG. 11). For this reason, for example, the inspection processing operation unit 61 measures pattern information using the image A. For example, a line width, a space width, and edge coordinates (E), of a pattern are calculated by the following: a change in gray-scale value in X, Y directions using the image A; detection of an edge; and the like. Then, the calculated information is stored in the auxiliary storage device 63 as inspection results.

It is to be noted that before the above-mentioned processing, filtering for enhancement or smoothing of an edge may also be performed in order to create a state of the image suitable for inspection. Filters used for the filtering can include a wiener filter, a constrained least squares filter, a projection filter and the like, which are used for restoration of a degraded image including defocus, distortion, etc., and a local average filter, a median filter, smoothing by a relaxation method, and the like, which are used for eliminating a noise component.

In the next place, for example, the defect severity judging unit 68 performs the next processing on the basis of the relation between the defect information (inspection-result information) 21 stored as inspection result in the auxiliary storage device 63 and information about wiring patterns, and then sets or determines a defect label before storing the defect label as data used for selecting the priority order of review, for example, in the auxiliary storage device 63.

In the case of the defects 150, 151, as the relation between a defect position and a wiring pattern, formula 1 and formula 2 described below hold. Accordingly, in appearance, it is found out that the defect 150 is in contact with a wiring pattern while the defect 151 is not contact with the wiring pattern. A label of each defect can be determined using the result. The defect 150 may also be judged to be a failure; and the defect 151 may also be judged to be a good item.

Defect 150: $(CX150-LX150/2) < E1, E2 < (CX150+LX150/2)$ (Formula 1)

Defect 151: $E3 < (CX151-LX151/2), (CX151+LX151/2) < E4$ (Formula 2)

Likewise, a judgment is also possible by the following method. Directional derivative (first differentiation) in four directions in total (a x direction, a y direction, and two directions having an angle of 45° with reference to x, y) is performed for all pixels of the image B corresponding to the pixels which have been judged to be the defect in the image A to determine maximum and minimum values for each. If the maximum value>0, the minimum value<0, |maximum value|>a constant value, |minimum value|>a constant value, it is possible to judge that a defect width is wider than or equal to a wiring width.

Alternatively, the judgment can also be made by the following steps: as is the case with the above-mentioned method, for all pixels corresponding to the defect in the images A, B, determining the average of gray-scale values on an image basis; and checking whether or not its difference exceeds a predetermined constant value. Parameters to be compared may include maximum and minimum values of brightness of each image, the sum total of differential values (or the average), a maximum value of differential values, and a standard deviation.

As described above, it is also possible to judge the criticality of a defect with higher accuracy by using a wiring pattern image as a substitute for the design layout information to examine directly the relation between the wiring pattern image and the defect in detail so as to label the defect.

This permits a defect that has a high possibility of influencing a yield to be efficiently reviewed by priority, whereby a direct factor exerting the influence can be identified in a short period of time and measures against the factor can be taken easily. Consequently, time taken to produce a defective unit is shortened, which leads to an improvement in yield.

Moreover, the methods for the reinspection processing (processing of the relation between the defect information (inspection-result information) 21 and wiring pattern information) include the following, as shown in FIG. 12: (a) a method in which reinspection processing 124 is performed using the same inspection processing unit as that of the inspection on the basis of an image (defect image) 125 having the appropriate size, including coordinates of a defect, which is obtained from defect information (defect center coordinates (CX, CY), defect size (area S; X, Y lengths LX, LY; etc.) 21 of the inspection and from an image memory 122 after the inspection processing 123 is completed in the inspection processing operation unit 61; (b) a method in which the inspection processing 123 and the reinspection processing 124 are performed in parallel (in a multitasking manner) in the same inspection processing operation unit 61; and (c) a method in which the inspection processing 123 is performed in the inspection processing operation unit 61a, and the reinspection processing 124 is performed in a dedicated reinspection processing operation unit 61b on the basis of the defect information 21 and the defect image 125. It is to be noted that the detected image and the reference image are acquired by the image acquiring unit 67 (121) before the acquired images are stored in the inspection processing operation unit 61 or the image memory 122 provided outside.

Next, an embodiment of how to select the priority order of review on the basis of a label which has been set for each defect in the defect severity judging unit 68, and on the basis of the number of defects for each label, will be described. To be more specific, review conditions used for selecting the priority order of review can be freely set by a user. The review conditions include the following: a condition in which only a defect having the size larger than or equal to a predetermined value or having the size smaller than or equal to the predetermined value is extracted; a condition in which only a defect existing in a given LSI function block is extracted; and a condition in which the given number of defects are extract from each LSI function block. In addition, a combination of those conditions may also be used. A merit of these conditions is that from among many defects detected by the inspection tool 60, it is possible to select efficiently a defect which causes an electric failure. A practical and significant review condition is that a defect which does not influence a yield is excluded from objects to be reviewed while a defect which will influence a yield is selected.

Figure 13:
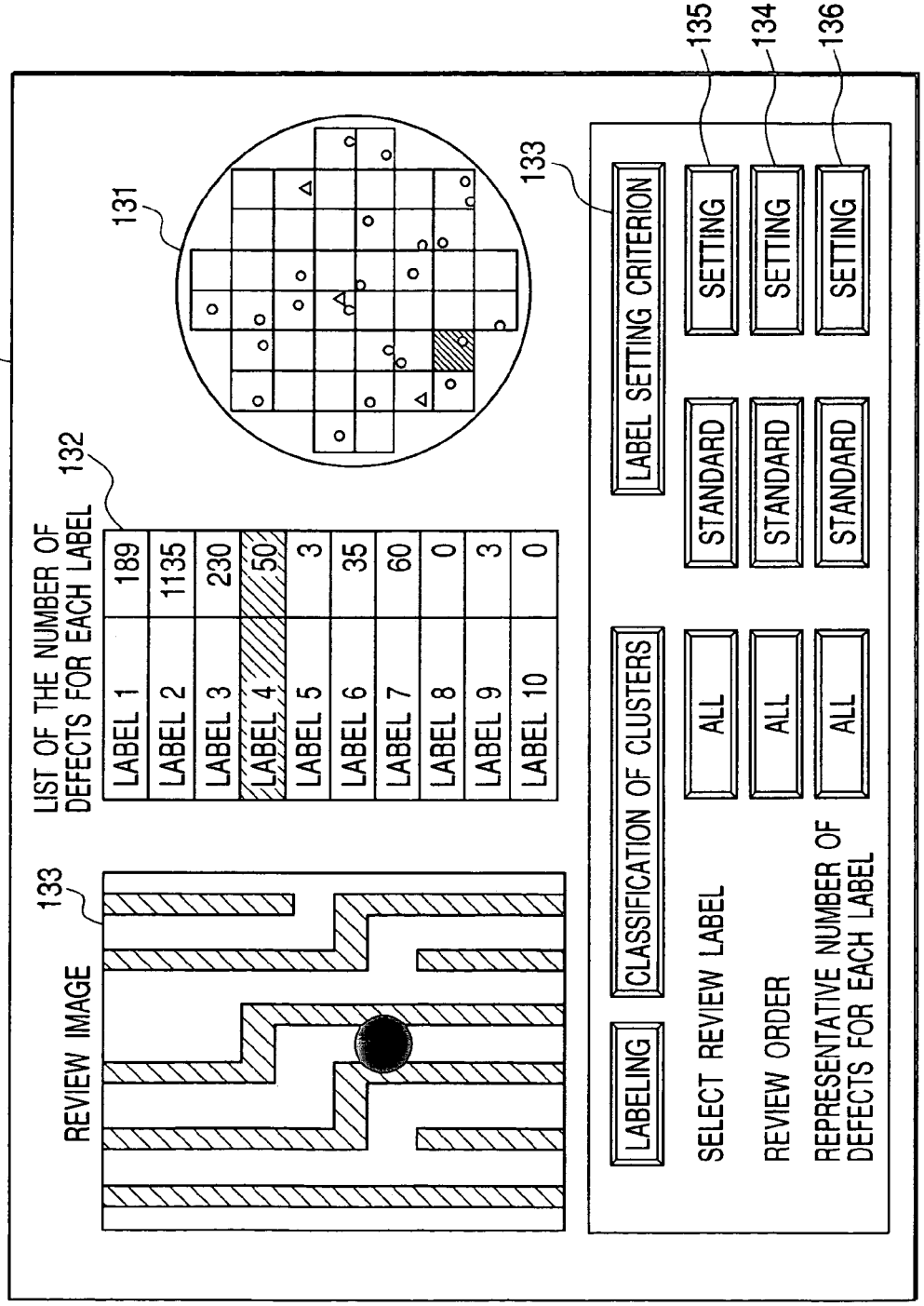
FIG. 13 is a diagram illustrating an example of a review screen which is one of display screens of a user interface in an inspection tool according to the present invention.

FIG. 13 illustrates an example of a review screen 130 displayed in the user interface 64 from the defect severity-judging unit 68. In this figure, wafer map data of a certain kind of wafer in a certain manufacturing process is displayed. In this example, in the upper right portion of the review screen 130, wafer map data 131 obtained from the inspection processing operation unit 61 is displayed; in the upper left portion, a magnifying image (review image) 133 of a labeled defect obtained from the image acquiring unit 67 is displayed; and in the center of the upper portion, how all defects have been labeled in the defect severity judging unit 68, and a list of the number of defects for each label 132, are displayed. The map data in a chip shown in FIG. 10, which is indicated with the reference numeral 36, may also be used as the wafer map data 131; and the magnifying image of a defect show in FIG. 10, which is indicated with the reference numeral 37, may also be used as the magnifying image (review image) 133 of the defect. More specifically, a large defect can also be reviewed using the inspection tool 60 by displaying the magnifying image (review image) 133 of the defect on the review screen 130.

In a window in the lower portion of the screen, basic menus and buttons used for condition settings of review are arranged. Conditions which can be set here are selection of labels to be reviewed, the review order of the labels, and the number of defects to be reviewed for each label. Each condition has setting buttons of All, Standard, and Setting. Pressing each setting button displays an individual setting screen.

FIG. 14 illustrates an example of a screen displayed when pressing a label setting criterion button 133 on the screen in FIG. 13. This setting screen 140 displays a menu by which the relation between a line width of a pattern and the defect size can be arbitrarily set regardless of the flow described in FIG. 8. After arbitrarily setting some labels, pressing a consistency check button 141 automatically executes consistency check as to whether or not the label conditions which have been set overlap one another and whether or not the settings lack a required label condition.

FIG. 15 illustrates a screen used for setting the label reviewing order, which is displayed when pressing a setting button 134 of review order shown in FIG. 13.

FIG. 16 illustrates a screen used for making a selection of whether or not each label is reviewed, which is displayed when pressing a setting button 135 of review label selection shown in FIG. 13.

FIG. 17 illustrates an example of a screen on which it is possible to set all of the review label selection, the review order, and the representative number of defects for each label. The number of detected defects for each label is also displayed at the same time.

In the above-mentioned description, a method in which a LSI chip area is divided into function blocks to sample a defect using pattern density information of each function block has been described. However, if the inspection tool 60 detects defect coordinates with a high degree of accuracy, a more effective method comprises the steps of: instead of pattern density information, creating a drawing image of a pattern itself for each LSI function block in a chip using circuit layout information; superimposing defect information on the image; and judging the criticality of the defect on the basis of formula 1 and formula 2 described above to label the defect.

Figure 18:
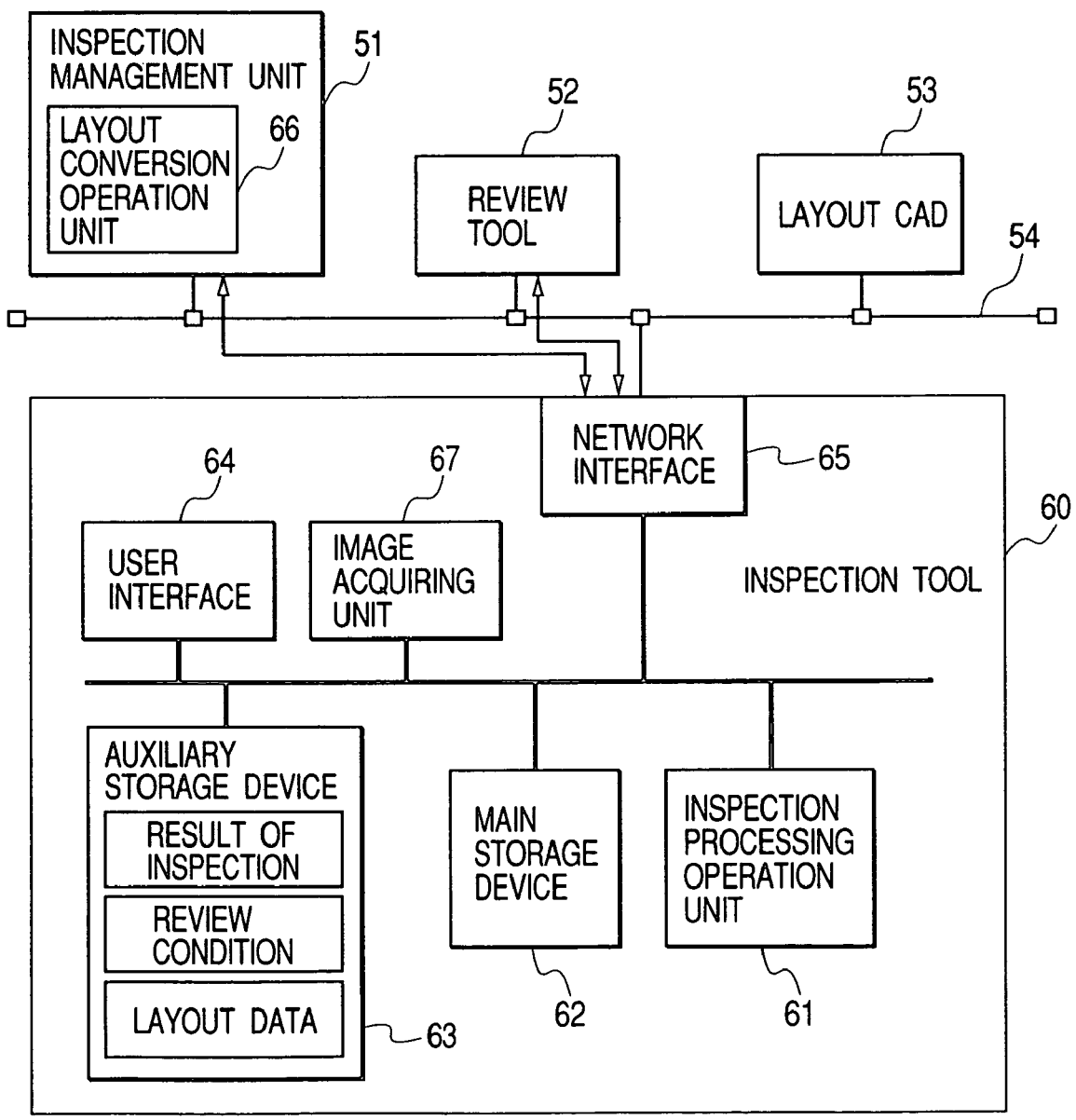
FIG. 18 is a block diagram illustrating a system configuration according to another embodiment of the present invention.
Figure 19:
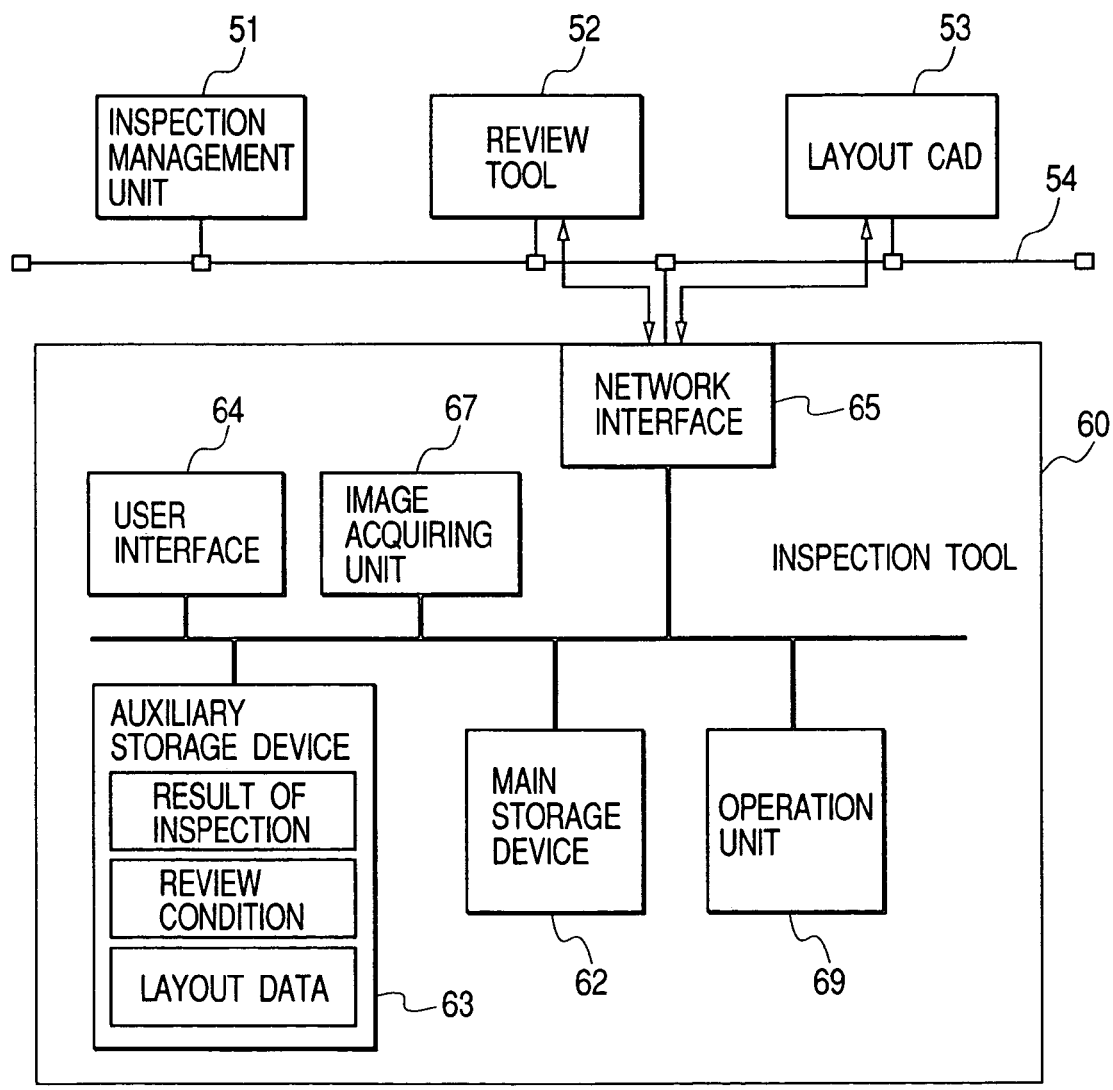
FIG. 19 is a block diagram illustrating a system configuration according to another embodiment of the present invention.

In addition, in the above-mentioned description, the defect severity-judging unit 68 for labeling each defect is placed in the inspection tool 60. However, such placement is not always required. The defect severity-judging unit 68 may also be placed in the inspection management unit 51. In this case, a label can be given to inspection result obtained from the same kind of inspection tool using the same review conditions. In addition, although the layout conversion operation unit 66 for obtaining circuit layout pattern information and pattern density data was also placed in the inspection tool 60, such placement is not always required. As shown in FIG. 18, the layout conversion operation unit 66 may also be placed in the inspection management unit 51, and converted layout information may also be transmitted to the auxiliary storage device 63 of the inspection tool 60 via the network 54, or to the main storage device 62. Moreover, the defect severity judging unit 68 and the layout conversion operation unit 66 may also be placed in the inspection management unit 51. Further, as shown in FIG. 19, inspection-processing operation, layout conversion operation, and defect severity judgment may also be performed in an operation unit 69 of the inspection tool 60.

In the embodiment described with reference to FIGS. 1, 18, and 19, the image-acquiring unit 67 acquires an image of detected defects such as a circuit pattern defect, a particle and a flaw to store temporarily the image in the main storage device 62. After that, the inspection processing operation unit 61 reads the image data stored in the main storage device, aligns the inspection image with the reference image to compare the images, and thereby detects a difference between the images as a defect.

Figure 20:
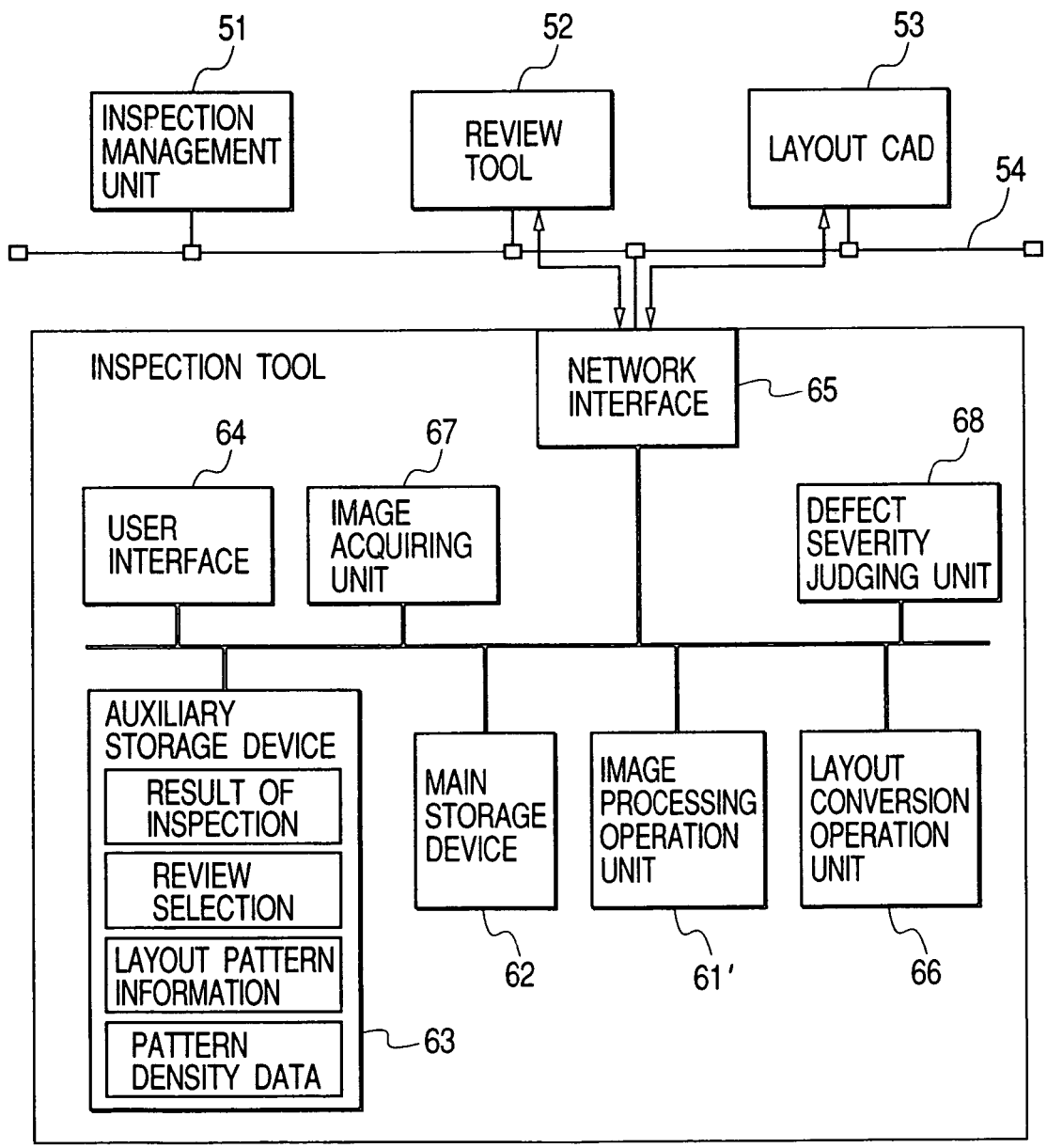
FIG. 20 is a block diagram illustrating a system configuration according to another embodiment of the present invention.

However, an image acquired by the image-acquiring unit 67 may be immediately compared with a reference image to detect a defect without using the main storage device. FIG. 20 illustrates its configuration.

In the configuration shown in FIG. 20, the image-acquiring unit 67 illuminates a light beam, which includes UV light and DUV light, or a charged particle beam on an object to be inspected such as a semiconductor wafer where a LSI such as a system LSI is formed. After that, the image acquiring unit 67 detects reflected light, or a reflected or transmitted charged particle, coming from the object to be inspected, using a detector, and then acquires an image of the object to be inspected. This acquired image includes a defect image such as a circuit pattern defect, a particle, and a flaw, generated on the object to be inspected.

The image acquired by the image acquiring unit 67 is transferred to an image processing operation unit 61'. The image processing operation unit 61' aligns the detected image transferred from the image acquiring unit 67 with a reference image before comparing the images. It is to be noted that the reference image is created from the detected image transferred from the image-acquiring unit 67. To be more specific, the detected pattern image which has been transferred before is temporarily stored in a memory, and this stored detected image is used as a reference image for a detected image transferred this time having a picked-up pattern which should be naturally the same as that in the reference image.

The detected image is compared with the reference image to detect a mismatch between both of the images as a defect candidate. Then, inspection result data including a position of the detected defect candidate and its size (an area, a projected length with reference to the X, Y axes, etc.) is detected. The inspection result data is stored in the auxiliary storage device 63.

The inspection result data stored in the auxiliary storage device 63 is processed using a method similar to that described in FIG. 1. After that, the criticality of a defect is judged to perform labeling so that the priority order of review can be selected.

As described above, the defect severity judging unit 68 can create data regarding the labeling performed on the basis of the relation between the defect size (area S; X, Y lengths LX, LY; etc.) and pattern density data (a line width, a space width, etc.), and regarding the number of defects, for each LSI function block in a chip, and can provide the review tool 52 with the data. This permits the review tool 52 to select easily a defect which should be reviewed by priority in a LSI item in which various circuit function blocks exist.

In addition, in the above description, the method for labeling a defect using only layout information about a manufacturing process relating to inspection has been described. However, not only using the layout information of the manufacturing process but also superimposing layout information before the manufacturing process (lower layout information) enables defect labeling in wiring data of other manufacturing processes (lower manufacturing process). Likewise, even if a possibility of a defect is low in the manufacturing process, if there is a possibility of a defect in a manufacturing process afterward (upper manufacturing process), such a possibility can also be estimated.

As described above, while inspecting a particle and a pattern defect in a piece of work which constitutes an electronic device, sampling a defect for which there is a high possibility of causing an electrical failure, and reviewing the defect by priority, enable more efficient inspection as compared with the conventional method.

Like a system LSI in particular, for a LSI item in which various circuit function blocks exist, judging a defect which should be reviewed by priority is essential to an early improvement in yield.

According to the present invention, using layout information permits a defect which should be reviewed by priority to be judged, which produces an effect that efficiency of inspection can be improved.

According to the present invention, as a result of the measures efficiently taken against a failure, an effect is produced that a yield of a semiconductor device can be improved.

The invention may be embodied in other specific forms without departing from the sprit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An inspection apparatus comprising:
   an image acquiring unit which inspects an object on which a circuit pattern is formed so as to acquire an image including a defect of the object;
   an image storage unit which stores the image including the defect, acquired by the image acquiring unit;
   an inspection processing operation unit which detects at least a defect by comparing the image including the defect stored in the image storage with a reference image, so as to extract inspection data including information about a position and a size of each detected defect;
   an input unit which inputs data from a CAD data base of detailed layout patterns of components of the object by converting said data from said CAD data base into circuit layout pattern information;

a graphical user interface unit which displays a screen for setting a label to classify each detected defect, a screen for selecting a label to be reviewed, a screen for setting an order for reviewing the labeled defects, and a screen for displaying a defect map and an enlarged image of the reviewed defect; and a judging unit which judges a priority of review of each detected defect by subsequently comparing the information about position and size of each detected defect already extracted from the inspection processing operation unit, with information of a width and pitch of patterns which are background to the defect extracted from the circuit layout pattern converted from the CAD database, and giving a higher priority to a defect having a size which is larger than: an accumulated size of a width of the pattern and a pitch of the pattern, and either one of a larger size among the pattern and the pattern pitch, than to a defect having a size which is smaller.

2. An inspection apparatus according to claim 1, wherein the judging unit is capable of displaying a wafer map of the object to be inspected on a display screen.

3. An inspection apparatus according to claim 1, wherein the input unit inputs the data of the detailed layout patterns of the components from a display screen on which a pattern image is displayed.

4. An inspection apparatus according to claim 1, wherein the data of the detailed layout patterns of the components includes information about position and size of each component, and the judging unit judges a priority of review of each detected defect by subsequently comparing the information about position and size thereof with the information about at least one of position and size of ones of the components.

5. An inspection apparatus according to claim 1, wherein the judging unit judges the priority of review from a criticality of each detected defect after analysis using the information about position and size thereof compared with the data of said detailed layout patterns of the object.

6. An inspection method comprising:

inspecting an object on which a circuit pattern is formed so as to acquire an image of the object including a defect;

storing the acquired image in a memory;

comparing the image stored in the memory with a reference image to detect an image of a defect candidate;

extracting inspection data including information about a position and a size of the defect from the detected image of the defect candidate;

inputting detailed layout pattern information of components of the object by converting data from a CAD data base into circuit layout pattern information;

displaying on a screen a set of buttons for setting review conditions on the screen, said buttons include a button for selecting a screen to input conditions for labeling the detected defect candidates, a button for selecting labeled defect candidates to be reviewed, and a button for setting an order for review; and judging a priority of review of each detected defect by subsequently comparing the information about position and size of each detected defect already extracted from the extracting operation, with information of a width and pitch of patterns which are background to the defect extracted from the detailed layout pattern converted from the CAD database, and giving a higher priority to a defect having a size which is larger than: an accumulated size of a width of the pattern and a pitch of the pattern, and either one of a larger size among the pattern and the pattern pitch, than to a defect having a size which is smaller.

7. An inspection method according to claim 6, wherein an image of the defect, which should be reviewed by priority order, is displayed on a display screen.

8. An inspection method according to claim 6, wherein a wafer map of the object to be inspected, is displayed on a display screen.

9. An inspection method according to claim 6, wherein the inputting includes inputting the data of the detailed layout pattern information of the components from a display screen on which a pattern image is displayed.

10. An inspection method according to claim 6, wherein the detailed layout pattern information of the components includes information about position and size of each component, and judging judges priority of review of each detected defect by using the information about position and size thereof compared with the information about at least one of position and size of ones of the components.

11. An inspection method according to claim 6, wherein in the operation of judging, the priority of review is judged from a criticality of each detected defect after analysis using the information about position and size thereof compared with the data of said detailed layout patterns of the object.

12. An inspection apparatus comprising:

an image acquiring unit which inspects an object on which a circuit pattern is formed so as to acquire an image including a defect of the object;

an image storage unit which stores the image including the defect acquired by the image acquiring unit;

an inspection processing operation unit which detects at least a defect by comparing the image including the defect stored in the image storage with a reference image, so as to extract inspection data including information about a position and a size of each detected defect;

an input unit which inputs data from an engineering design data base of detailed layout patterns of components of the object by converting said data from said engineering design data base into circuit layout pattern information;

a graphical user interface unit which displays a screen for setting a label to classify each detected defect, a screen for selecting a label to be reviewed, a screen for setting an order for reviewing the labeled defects, and a screen for displaying a defect map and an enlarged image of the reviewed defect; and a judging unit which judges a priority of review of each detected defect by subsequently comparing the information about position and size of each detected defect already extracted from the inspection processing operation unit, with information of a width and pitch of patterns which are background of the defect extracted from the circuit layout pattern converted from the CAD database, and giving a higher priority to a defect having a size which is larger than: an accumulated size of a width of the pattern and a pitch of the pattern, and either one of a larger size among the pattern and the pattern pitch, than to a defect having a size which is smaller.

13. An inspection apparatus according to claim 12, wherein the judging unit is capable of displaying a wafer map of the object to be inspected on a display screen.

14. An inspection apparatus according to claim 12, wherein the input unit inputs the data of the detailed layout patterns of the components from a display screen on which a pattern image is displayed.

15. An inspection apparatus according to claim 12, wherein the data of the detailed layout patterns of the components includes information about position and size of each component, and the judging unit judges the priority of review of each detected defect by using the information about position and size thereof and subsequently comparing with the information about at least one of position and size of ones of the components.

16. An inspection apparatus according to claim 12, wherein the judging unit judges the priority of review from a criticality of each detected defect after analysis using the information about position and size thereof compared with the data of said detailed layout patterns of the object.

17. An inspection method comprising:
inspecting an object on which a circuit pattern is formed so as to acquire an image of the object including a defect;
storing the acquired image in a memory;
comparing the image stored in the memory with a reference image to detect an image of a defect candidate;
extracting inspection data including information about a position and a size of the defect from the detected image of the defect candidate;
inputting detailed layout pattern information of components of the object by converting data from a engineering design data base into circuit layout pattern information;
displaying on a screen a set of buttons for setting review conditions on the screen, said buttons include a button for selecting a screen to input conditions for labeling the detected defect candidates, a button for selecting labeled defect candidates to be reviewed, and a button for setting an order for review; and
judging a priority of review of each detected defect by subsequently comparing the information about position and size of each detected defect already extracted from the extracting operation, with information of a width and pitch of patterns which are background to the defect extracted from the detailed layout pattern converted from the CAD database, and giving a higher priority to a defect having a size which is larger than: an accumulated size of a width of the pattern and a pitch of the pattern, and either one of a larger size among the pattern and the pattern pitch, than to a defect having a size which is smaller.

18. An inspection method according to claim 17, wherein an image of the defect, which should be reviewed by priority order, is displayed on a display screen.

19. An inspection method according to claim 17, wherein a wafer map of the object to be inspected, is displayed on a display screen.

20. An inspection method according to claim 17, wherein the inputting includes inputting the data of the detailed layout pattern information of the components from a display screen on which a pattern image is displayed.

21. An inspection method according to claim 17, wherein the detailed layout pattern information of the components includes information about position and size of each component, and judging judges the priority of review of each detected defect by using the information about position and size thereof compared with the information about at least one of position and size of ones of the components.

22. An inspection method according to claim 17, wherein in the operation of judging, the priority of review is judged from a criticality of each detected defect after analysis using the information about position and size thereof compared with the data of said detailed layout patterns of the object.

* * * * *